United States Patent [19]

Zupancic et al.

[11] Patent Number: 4,551,525

[45] Date of Patent: Nov. 5, 1985

[54] PROCESS FOR PREPARING N-(2-PYRIDYL)-2-METHYL-4-HYDROXY-2H-1,2-BENZOTHIAZINE-3-CARBOXAMIDE-1,1-DIOXIDE

[75] Inventors: Natasa Zupancic; Boris Sket, both of Ljubljana; Pavel Zupet, Novo mesto; Marko Zupan, Ljubljana, all of Yugoslavia

[73] Assignee: KRKA, tovarna zdravil, n.sol.o., Novo mesto, Yugoslavia

[21] Appl. No.: 656,850

[22] Filed: Oct. 2, 1984

[30] Foreign Application Priority Data

Oct. 6, 1983 [YU] Yugoslavia .......................... 2021/83

[51] Int. Cl.$^4$ ........................................... C07D 401/12
[52] U.S. Cl. ...................................................... 544/49
[58] Field of Search ........................................... 544/49

[56] References Cited

U.S. PATENT DOCUMENTS

| 4,474,955 | 10/1984 | Iannella | 544/49 |
| 4,474,956 | 10/1984 | Zirngibl et al. | 544/49 |
| 4,478,996 | 10/1984 | Almenara | 544/49 |
| 4,483,982 | 11/1984 | Weeks | 544/49 |

*Primary Examiner*—John M. Ford
*Attorney, Agent, or Firm*—Pollock, Vande Sande & Priddy

[57] ABSTRACT

A process for preparing N-(2-pyridyl)-2-methyl-4-hydroxy-2H-1,2-benzothiazine-3-carboxamide-1,1-dioxide which comprises reacting an alkyl-4-hydroxy-2-methyl-2H-1,2-benzothiazine-3-carboxylate-1,1-dioxide with P-phenyl-N,N'-di-2-pyridylphosphonium diamide.

8 Claims, No Drawings

PROCESS FOR PREPARING N-(2-PYRIDYL)-2-METHYL-4-HYDROXY-2H-1,2-BENZOTHIAZINE-3-CARBOXAMIDE-1,1-DIOXIDE

TECHNICAL FIELD OF THE INVENTION

The present invention relates to a novel process for preparing N-(2-pyridyl)-2-methyl-4-hydroxy-2H-1,2-benzothiazine-3-carboxamide-1,1-dioxide of the formula

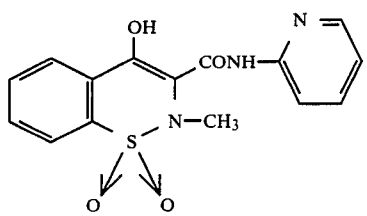

The compounds of this kind are well-known non-steroid anti-inflammatory agents. They exhibit an anti-inflammatory and antipyretic action and are used in the therapy of various rheumatic diseases. The mechanism of action is based upon inhibition of synthesis of prostaglandins causing inflammations in human organism. The pharmaceutical compositions are administered perorally or parenterally.

TECHNICAL PROBLEM

There was a need to develop an improved process for preparing the compound I, e.g. in which process the reaction time would be shorter and yields greater. The basis of the invention is therefore a novel amidating process employing a novel agent, not disclosed in the Prior Art patent applications for preparing the compound I.

PRIOR ART

The preparation of compound I is described in literature, i.e. in U.S. Pat. No. 3,591,584 as a reaction of 3,4-dihydro-2-methyl-4-oxo-2H-1,2-benzothiazine-1,1-dioxide with 2-amino-pyridyl isocyanate, in U.S. Pat. No. 3,891,637 as a transamidating reaction of 4-hydroxy-2-methyl-2H-1,2-benzothiazine-3-carboxanilide with 2-aminopyridine, in U.S. Pat. No. 3,853,862 as cyclization of N-methyl-N'-benzyloxycarbonyl-N-(2-pyridyl)glycinamide, and in U.S. Pat. No. 4,100,347 as a preparation of acid chloride of 4-hydroxy-2-methyl-2H-1,2-benzothiazine-3-carboxylic acid and its condensation with 2-aminopyridine as well as in U.S. Pat. No. 3,591,584, wherein methyl-4-hydroxy-2-methyl-2H-1,2-benzothiazine-3-carboxylate-1,1-dioxide is amidated with 2-aminopyridine.

THE DESCRIPTION OF THE SOLUTION OF THE TECHNICAL PROBLEM WITH EXAMPLES

The process according to the invention is characterized in that alkyl-4-hydroxy-2-methyl-2H-1,2-benzothiazine-3-carboxylate-1,1-dioxide of the formula II

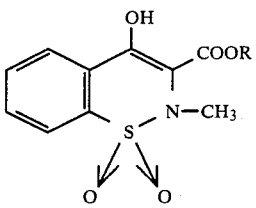

wherein R represents an alkyl group with 1 to 4 carbon atoms, as methyl, ethyl, propyl, tert. butyl group, is reacted with P-phenyl-N,N'-di-2-pyridylphosphonium diamide of the formula III

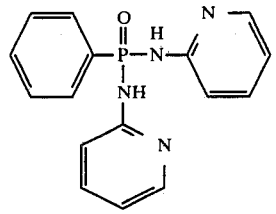

to obtain a compound I.

The amidation is carried out in inert organic solvents, preferably in xylene and o-xylene. The reaction is executed at the reflux temperature of the reaction mixture, i.e. from 135° to 145° C.

The obtained crude N-(2-pyridyl)-2-alkyl-4-hydroxy-2H-1,2-benzothiazine-2-carboxamide-1,1-dioxide is purified by means of recrystallization, e.g. from a (1:1) acetone-methanol mixture or (1:1) acetone-isopropanol mixture.

A process for preparing the compound of the formula III, i.e. P-phenyl-N,N'-di-2-pyridyl-phosphonium diamide, is disclosed in Monatsh. Chem. 91 (1960), 836.

The compound II, i.e. alkyl-4-hydroxy-2-methyl-2H-1,2-benzothiazine-3-carboxylate-1,1-dioxide, is commercially available.

The present process of amidating compound II with P-phenyl-N,N'-di-2-pyridyl-phosphonium diamide is new and not described in any literature.

The advantages of the present process are as follows:

(a) Much shorter reaction times in comparison with Prior Art processes.

(b) For removal of alcohol, e.g. methanol, there is no need to use molecular sieves since at the reaction there is formed P-phenyl-di-methyl ester of phosphonic acid of the formula IV

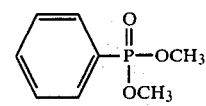

(c) The employed agent of the formula III is not hygroscopic and is odourless, thus it is more stable and its transport is easier (2-aminopyridine, which is normally used, has a penetrating odour and is very hygroscopic and thus there is a risk of undesired hydrolysis of the starting substance).

The invention is illustrated in more detail by the following Examples, which should in no way limit the scope of the invention.

EXAMPLE 1

2.69 g (0.01 mole) of methyl-4-hydroxy-2-methyl-2H-1,2-benzothiazine-3-carboxylate-1,1-dioxide and 3.10 g (0.01 mole) of P-phenyl-N,N'-di-2-pyridyl-phosphonium diamide are suspended in 600 ml of xylene (puriss. p.a.) and heated under reflux for 7.5 hours, when the reaction is completed (followed by TLC: $SiO_2$, mobile phase ethanol-chloroform 96:4). The solvent is evaporated on rotavapor in vacuo, the oily residue is suspended in 20 ml of ethanol and the product which precipitates is filtered by suction.

There is obtained N-(2-pyridyl)-2-methyl-4-hydroxy-2H-1,2-benzothiazine-3-carboxamide-1,1-dioxide (2.48 g, 75%), m.p. 198°–201° C. The spectroscopic data are in accordance with the literature data.

EXAMPLE 2

2.69 g (0.01 mole) of methyl-4-hydroxy-2-methyl-2H-1,2-benzothiazine-3-carboxylate-1,1-dioxide and 3.10 g (0.01 mole) of P-phenyl-N,N'-di-2-pyridyl-phosphonium diamide are suspended in 600 ml of o-xylene and heated under reflux. After 6 hours the reaction is completed (followed by TLC: $SiO_2$, mobile phase ethanol-chloroform 96:4). The solvent is then evaporated on rotavapor in vacuo, the oily residue is suspended in 20 ml of ethanol and the product which precipitates is filtered by suction.

There is obtained N-(2-pyridyl)-2-methyl-4-hydroxy-2H-1,2-benzothiazine-3-carboxamide-1,1-dioxide (2.35 g, 71%), m.p. 198°–201° C. The spectroscopic data are in accordance with the literature data.

Similar results are achieved when the compound II, wherein R represents ethyl, propyl or tert. butyl, is used.

What is claimed is:

1. A process for preparing N-(2-pyridyl)-2-methyl-4-hydroxy-2H-1,2-benzothiazine-3-carboxamide-1,1-dioxide of formula I

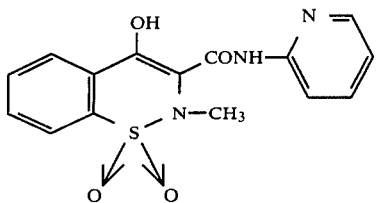

characterized in that alkyl-4-hydroxy-2-methyl-2H-1,2-benzothiazine-3-carboxylate-1,1-dioxide of the formula II

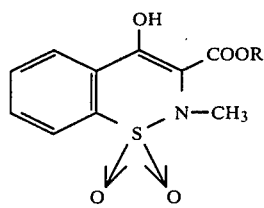

wherein R represents an alkyl group of 1 to 4 carbon atoms, is reacted with P-phenyl-N,N'-di-2-pyridyl-phosphonium diamide of the formula III

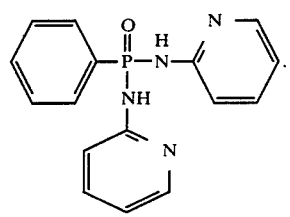

2. A process according to claim 1, characterized in that inert organic solvents are used as reaction medium.

3. A process according to claim 1 characterized in that the amidation reaction is carried out at the reflux temperature of the reaction mixture.

4. A process according to claim 2, characterized in that the amidation reaction is carried out at the reflux temperature of the reaction mixture.

5. The process of claim 2 wherein said solvent is xylene or o-xylene.

6. The process of claim 1 wherein R is methyl.

7. The process of claim 1 wherein the amidation reaction is carried out at a temperature of 135° C. to 145° C.

8. The process of claim 2 wherein the amidation reaction is carried out at a temperature of 135° C. to 145° C.

* * * * *